United States Patent
Allerdings et al.

(10) Patent No.: US 10,195,355 B2
(45) Date of Patent: Feb. 5, 2019

(54) SUPPLEMENTARY DEVICE FOR A MANUALLY OPERABLE INJECTION DEVICE

(71) Applicant: SANOFI-AVENTIS DEUTSCHLAND GMBH, Frankfurt am Main (DE)

(72) Inventors: Alexander Allerdings, Frankfurt am Main (DE); Martin Haupt, Vienna (AT); Erich Rittenbacher, Vienna (AT)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 505 days.

(21) Appl. No.: 14/783,171

(22) PCT Filed: Apr. 16, 2014

(86) PCT No.: PCT/EP2014/057786
§ 371 (c)(1),
(2) Date: Oct. 8, 2015

(87) PCT Pub. No.: WO2014/173773
PCT Pub. Date: Oct. 30, 2014

(65) Prior Publication Data
US 2016/0051762 A1 Feb. 25, 2016

(30) Foreign Application Priority Data
Apr. 22, 2013 (EP) .................................. 13164754

(51) Int. Cl.
*A61M 5/315* (2006.01)
*A61M 5/24* (2006.01)
*G06F 19/00* (2018.01)

(52) U.S. Cl.
CPC .......... *A61M 5/31535* (2013.01); *A61M 5/24* (2013.01); *A61M 2205/14* (2013.01);
(Continued)

(58) Field of Classification Search
CPC ........ A61M 2205/58; A61M 2205/581; A61M 2205/582; A61M 2205/6063;
(Continued)

(56) References Cited

U.S. PATENT DOCUMENTS

2013/0097822 A1* 4/2013 Mayberry ................ F16B 2/10
24/509

FOREIGN PATENT DOCUMENTS

EP            1897803      3/2008
JP     WO 2012120774 A1 * 9/2012 .......... H01M 2/1016
(Continued)

OTHER PUBLICATIONS

European Search Report for EP Application No. 13164754, completed Sep. 24, 2013.
(Continued)

*Primary Examiner* — Bhisma Mehta
*Assistant Examiner* — William Frehe
(74) *Attorney, Agent, or Firm* — Fish & Richardson P.C.

(57) ABSTRACT

The present invention relates to a supplementary device for a manually operable injection device. The device has a body and a mating unit configured to releasably mount the body to the injection device in a specific position relative to an outside surface of the injection device.

16 Claims, 12 Drawing Sheets

(52) U.S. Cl.
CPC ............... *A61M 2205/3592* (2013.01); *A61M 2205/502* (2013.01); *A61M 2205/52* (2013.01); *A61M 2205/58* (2013.01); *A61M 2205/581* (2013.01); *A61M 2205/582* (2013.01); *A61M 2205/6045* (2013.01); *A61M 2205/6063* (2013.01); *A61M 2205/6072* (2013.01); *A61M 2205/6081* (2013.01); *A61M 2209/04* (2013.01); *G06F 19/3468* (2013.01)

(58) Field of Classification Search
CPC ...... A61M 2209/04; A61M 2005/3152; A61M 2005/2006; F16B 2/10; F16B 5/4833; F16L 3/10; A61B 5/4833
See application file for complete search history.

(56) References Cited

FOREIGN PATENT DOCUMENTS

| | | | |
|---|---|---|---|
| WO | 2009/024562 | 2/2009 | |
| WO | 2010/037828 | 4/2010 | |
| WO | 2010/098927 | 9/2010 | |
| WO | 2011/117212 | 9/2011 | |
| WO | 2013/050535 | 4/2013 | |
| WO | 2013/120775 | 8/2013 | |
| WO | WO 2013120774 A1 * | 8/2013 | .............. A61M 5/24 |

OTHER PUBLICATIONS

International Search Report and Written Opinion for Int. App. No. PCT/EP2014/057786, dated Jun. 2, 2014.

* cited by examiner

SUPPLEMENTARY DEVICE FOR A MANUALLY OPERABLE INJECTION DEVICE

CROSS REFERENCE TO RELATED APPLICATIONS

The present application is a U.S. National Phase Application pursuant to 35 U.S.C. §371 of International Application No. PCT/EP2014/057786 filed Apr. 16, 2014, which claims priority to European Patent Application No. 13164754.7 filed Apr. 22, 2013. The entire disclosure contents of these applications are herewith incorporated by reference into the present application.

TECHNICAL FIELD

The present invention relates to an apparatus for supplementing a medical device configured to eject a medicament. In particular, the present invention relates to a supplementary device for a manually operable injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring.

It has been described, for instance in WO 2011/117212 to provide a supplementary device comprising a mating unit for releasably attaching the device to an injection device. The device includes a camera and is configured to perform optical character recognition (OCR) on captured images visible through a dosage window of the injection pen, thereby to determine a dose of medicament that has been dialled into the injection device.

SUMMARY

It is thus inter alia an object of the present invention to provide a supplementary device for a manually operable injection device.

According to a first aspect of embodiments of the present invention, there is provided a supplementary device for a manually operable injection device, the supplementary device comprising a body; and a mating unit configured to releasably mount the body to the injection device in a specific position relative to an outside surface of the injection device; wherein the mating unit comprises an engaging unit comprising an engaging arm configured to engage the supplementary device with the injection device and a resilient member configured to bias the engaging arm into engagement with the injection device.

This helps to ensure that the engaging unit reliably aligns and engages with the injection device.

The engaging arm may be rotatable between an engaged position and a detached position. With this arrangement it is possible to securely engage and release the engaging arm with the injection device, and to aid alignment of the engagement arm.

The supplementary device may further comprise a pivot axle defining a rotational axis about which the engaging arm is configured to rotate. Therefore, it is possible to ensure rotation of the engaging arm about a rotational axis. The engaging arm may rotate with the pivot axle, or the engaging arm may rotate about the pivot axle. The pivot axle may extend perpendicular to the engaging arm.

The resilient member may be on the pivot axle. This provides for a compact arrangement, and minimises the space required to provide biasing means.

The resilient member may be disposed eccentrically on the pivot axis. This means that the axis of rotation of the resilient member is offset from the axis of rotation of the engaging arm.

The resilient member may be a torsion spring. This allows for a compact arrangement. Alternative springs may be used as the resilient member.

The resilient member may be configured to act on the engaging arm proximate to or at a free end of the arm. This helps ensure that an effective biasing force acts on the engaging arm.

The engaging arm may have an engaging element at one end configured to engage with a corresponding engaging portion on the injection device when the body is disposed in a specific position relative to an outside surface of the injection device. The engaging element may be an engaging protrusion configured to engage in an indent, acting as an engaging portion, on the injection device when the body is disposed in a specific position relative to an outside surface of the injection device. Alternatively, the engaging element may be an engaging indent configured to engage with a protrusion, acting as an engaging portion, on the injection device when the body is disposed in a specific position relative to an outside surface of the injection device.

The engaging arm may have an actuating section configured to urge the engaging element away from the injection device. This aids removal of the supplementary device from an injection device.

The actuating section may be operated manually. That is, a user operates the actuating section thereby moving the engaging element or elements from an engaged position to a detached position. When the engaging element or elements are in their detached position, the supplemental device may be detached from the manually operable injection device.

The engaging arm may be a first engaging arm and the engaging unit may further comprise a second engaging arm. The free ends of the support members may be biased towards each other. This may provide a more effective engaging means.

The body may comprise a channel configured to receive part of the injection device. The engaging arm or each engaging arm may be configured to bias the injection device against a surface in the channel. This helps to ensure that the supplementary device does not move away from the injection device during use of the devices.

The mating unit may further comprise a collar extending from the body which is configured to receive an injection device so that the injection device extends through the collar.

The mating unit may further comprise first and second locating surfaces spaced from each other to receive an injection device therebetween. The collar may be configured to be pivoted between a first position in which an injection device is slidably receivable through the collar and a secured position in which the first and second locating surfaces are located against an outer surface of the injection device.

The engaging unit may be configured to engage with the injection device when the collar is pivoted into its secured position. The collar helps to maintain the supplementary device in a desired position and orientation on the injection device. The second locating surface may be disposed between the first locating surface and the engaging unit.

The mating unit may further comprise a locating recess in the body, the locating recess being configured to mate with a locating rib on the injection device.

The supplementary device may further comprise an optical reading arrangement. The optical reading arrangement may be directed at a display of the invention device when the body is mounted to the injection device in a specific position relative to an outside surface of the injection device.

According to another aspect of embodiments of the invention, there is provided a system comprising an injection device and a supplementary device.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
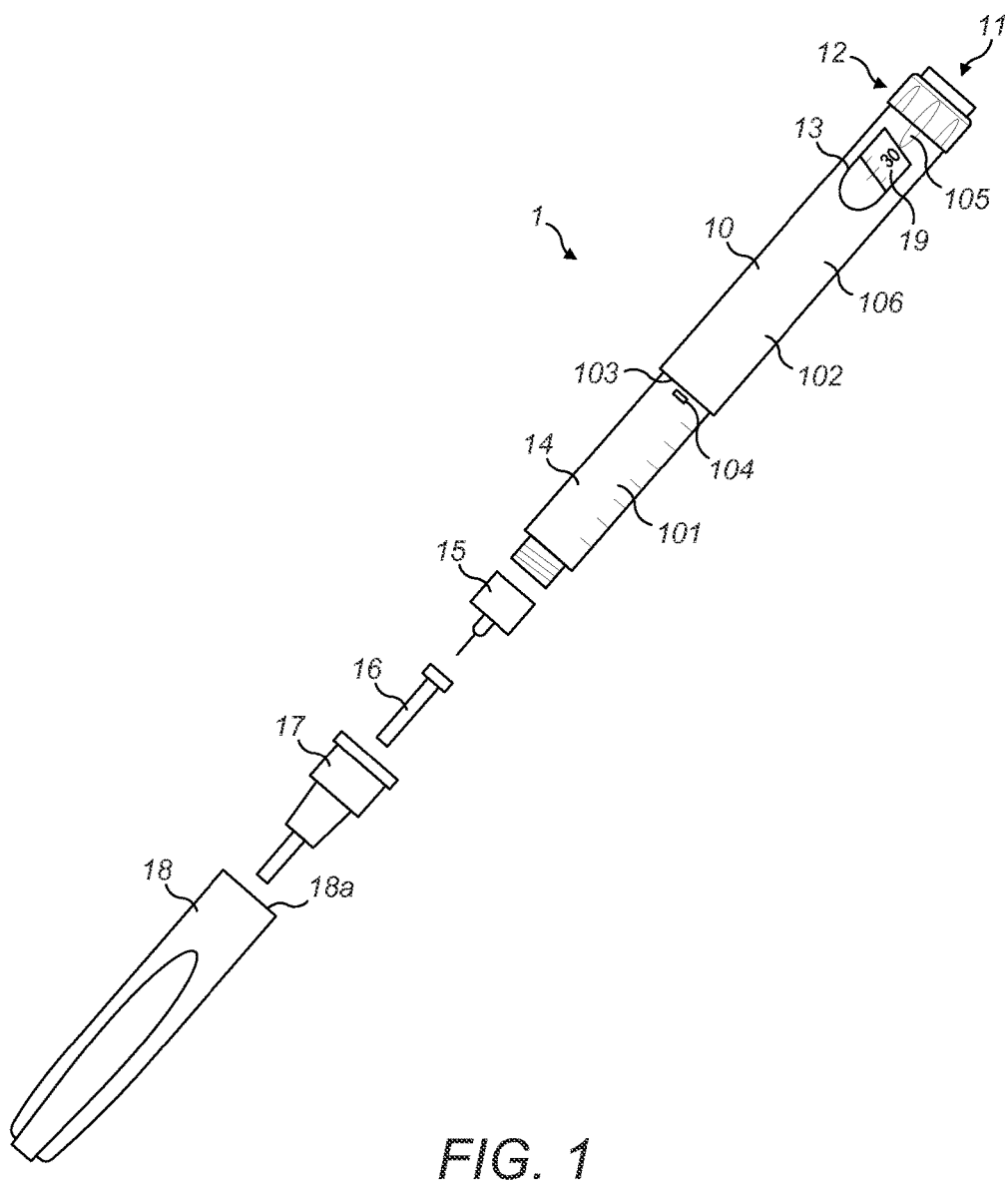
FIG. 1: an exploded view of an injection device.

FIG. 1 is an exploded view of an injection device 1, which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning a dosage knob 12, and the selected dose is then displayed via a dosage window or display 13, for instance in multiples of so-called International Units (IU), wherein one IU is the biological equivalent of about 45.5 micrograms of pure crystalline insulin (1/22 mg). An example of a selected dose displayed in dosage window or display 13 may for instance be 30 IUs, as shown in FIG. 1. It should be noted that the selected dose may equally well be displayed differently, for instance by an electronic display. It will be understood that dosage window relates to the section of the injection device through or on which the selected dosage is visible.

Turning the dosage knob 12 causes a mechanical click sound to provide acoustical feedback to a user. The numbers displayed in dosage window or display 13 are printed on a sleeve that is contained in housing 10 and mechanically interacts with a piston in insulin container 14. When needle 15 is stuck into a skin portion of a patient, and then injection button 11 is pushed, the insulin dose displayed in display 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

The housing 10 of the injection device 1 comprises a front section 101 and a rear section 102. The needle 15 is affixed to the front end of the front section 101 and the dosage knob 12 extends from the rear end of the rear section 102. The front section 101 has a smaller diameter than the rear section 102 of the injection device housing 10. A shoulder 103 is defined between the front section 101 and the rear section 102. The shoulder 103 extends circumferentially around the housing 10.

The cap 18 extends over the front section 101. The cap 18 covers the front section 101 and a lip 18a of the cap 18 locates against the shoulder 103.

A cap retaining ridge 104 is formed on the outer surface of the front section 101 of the housing 10 of the injection device 1. The cap retaining ridge 104 is disposed proximate to, but spaced from, the shoulder 103. The ridge 104 extends diametrically about the front section 101. The ridge 104 locates over one or more retaining elements (not shown) formed on the inner surface of the cap 18 to retain the cap 18 in position over the front section 101. Alternatively, the cap retaining ridge 104 locates in a corresponding circumferentially extending recess (not shown) formed on the inner surface of the cap 18.

The injection device 1 further comprises additional elements. A rib 105 protrudes from an outer surface 106 of the injection device 1. The rib 105 acts as an alignment element for locating the body in a specific position relative to the outer surface 106 of the injection device 1. The rib 105 upstands from the outer surface 106 of the injection device 1 between the dosage display 13 and the dosage knob 12. The dosage knob 12 is disposed on the rear section 102 of the injection device housing 10. The rib 105 is elongate and extends parallel to the longitudinal axis of the injection device 1.

Left and right indents 107 (refer to FIG. 8) are formed in the outer surface 106 of the injection device 1. The two indents 107 are formed in the rear section 102. Each indent 107 is formed proximate to the rear end of the injection device housing 10. The indents 107 are formed generally diametrically opposite to each other on left and right sides of the injection device 1. The indents 107 have chamfered sides. Each indent may be a notch.

Figure 2A:
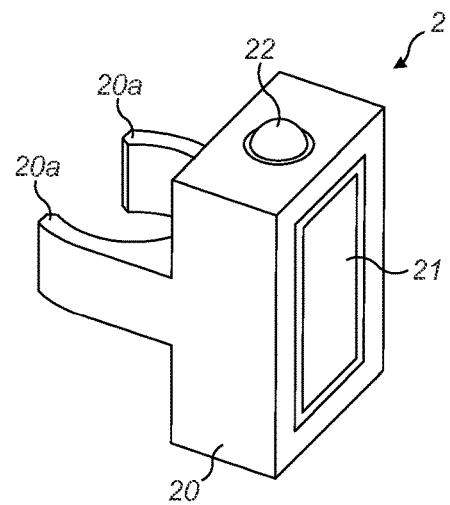
FIG. 2a: a schematic illustration of a supplementary device to be releasably attached to the injection device of FIG. 1 according to an embodiment of the present invention.

FIG. 2a is a schematic illustration of a supplementary device 2 to be releasably attached to injection device 1 of FIG. 1. FIG. 2a is highly schematic, and details of the physical arrangement of the supplementary device 2 are described below with reference to FIG. 2b. Supplementary device 2 comprises a housing 20 with a mating unit 20a configured to embrace the housing 10 of injection device 1 of FIG. 1, so that supplementary device 2 sits tightly on housing 10 of injection device 1, but is nevertheless removable from injection device 1, for instance when the injection device 1 is empty and has to be replaced.

Supplementary device 2 contains optical and acoustical sensors for gathering information from injection device 1. At least a part of this information, for instance a selected dose (and optionally a unit of this dose), is displayed via display unit 21 of supplementary device 2. The dosage display 13 of injection device 1 is obstructed by supplementary device 2 when attached to injection device 1.

Supplementary device 2 further comprises three user input transducers, illustrated schematically as a button 22. These input transducers allow a user to turn on/off supplementary device 2, to trigger actions (for instance to cause establishment of a connection to or a pairing with another device, and/or to trigger transmission of information from supplementary device 2 to another device), or to confirm something.

Figure 2B:
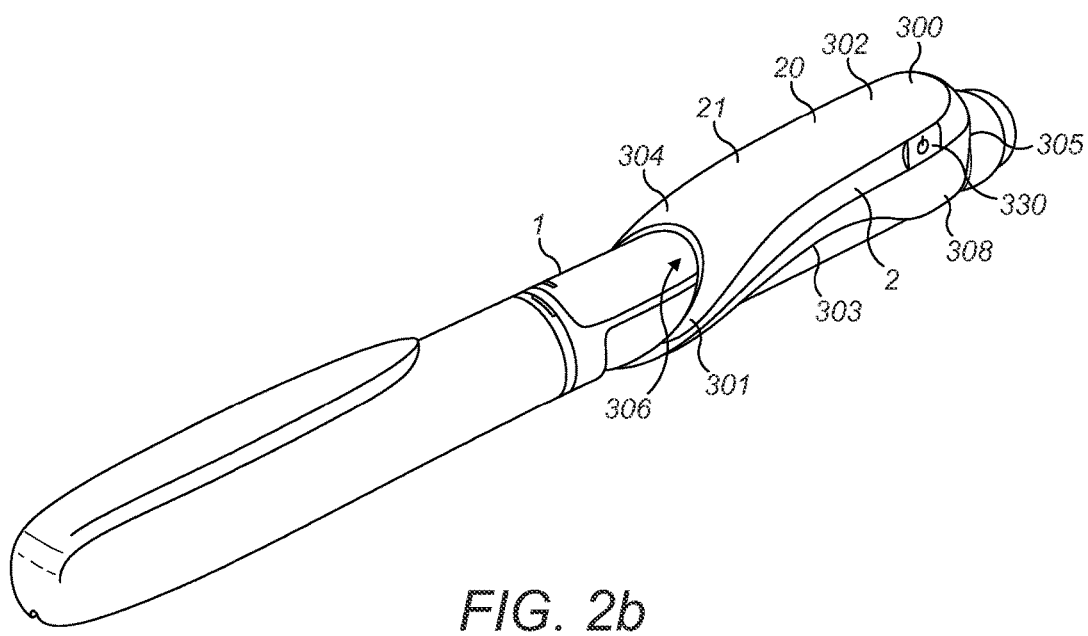
FIG. 2b: a perspective view of the supplementary device of FIG. 2a releasably attached to the injection device of FIG. 1.

FIG. 2b shows a view of the supplementary device 2 in greater detail. The supplementary device 2 is shown mounted to the injection device 1 in FIG. 2b.

The housing 20 of the supplementary device 2 has a body 300 and a collar 301. The body 300 is elongate and the display unit 21 is disposed on an upper side 302 of the body 300. The collar 301 extends from a lower side 303 of the body 300. The body 300 has a front end 304 and a rear end 305. The collar 301 extends from the front end 304. The collar 301 extends from the body 300 at an acute angle to the longitudinal axis of the elongate body 300.

Figure 11:
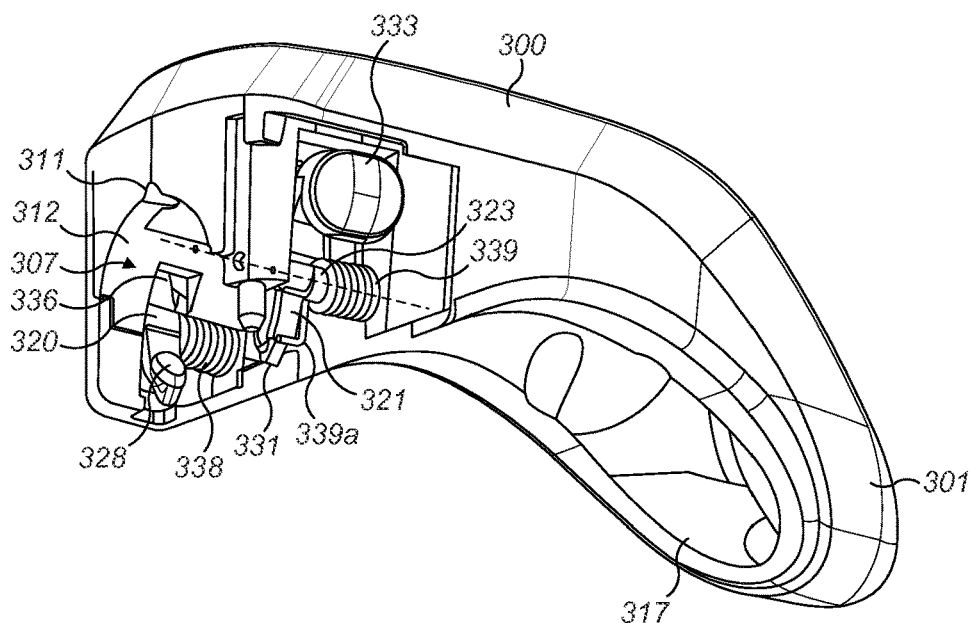
FIG. 11: a perspective view of the supplementary device shown in FIG. 2b with a wing omitted.

The collar 301 has an aperture 306 formed therethrough. The collar 301 is configured to receive the injection device 1 through the aperture 306. A channel 307 (refer to FIG. 11) is formed in the lower side 303 of the body 300. The channel 307 is elongate and extends between the front end 304 and the rear end 305 of the body 300.

Two wings 308, acting as protective walls, extend downwardly from the lower side 303 of the body 300. The wings 308 are spaced from each other and distend from either side of the channel 307. Therefore, the injection device 1 is receivable between the wings 308. The wings 308 are disposed at the rear end 305 of the body 300, at an opposite end of the body 300 to the collar 301.

The collar 301 and channel 307 form part of an alignment arrangement or alignment unit. The alignment unit is configured to locate the body in a specific position relative to the outside surface 106 of the injection device 1. The alignment unit forms part of the mating unit configured to embrace the housing 10 of injection device 1 to maintain the supplementary device in a specific position on the injection device 1.

The supplementary device 2 further comprises an engaging unit or arrangement configured to releasably mount the body to the injection device 1. The collar 301 also forms part of the engaging unit. The engagement unit forms part of the mating unit.

The features that contribute to correct alignment of the supplementary device 2 on the injection device 1 can be termed an alignment arrangement or alignment unit. The features that contribute to engagement of the supplementary device 2 to the injection device 1 can be termed an engaging unit or engaging arrangement.

Figure 3A:
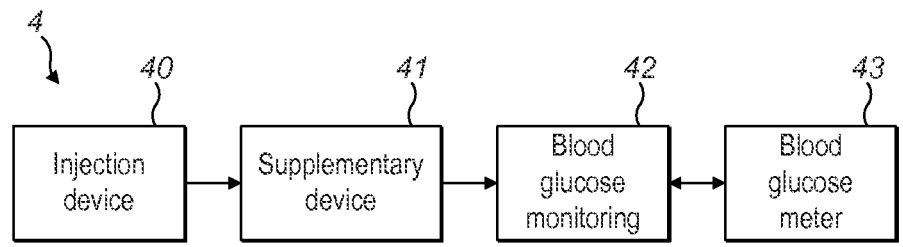
FIGS. 3A and 3b: possible distributions of functions among devices when using a supplementary device (such as the supplementary devices of FIGS. 2a and 2b) together with an injection device.
Figure 3B:
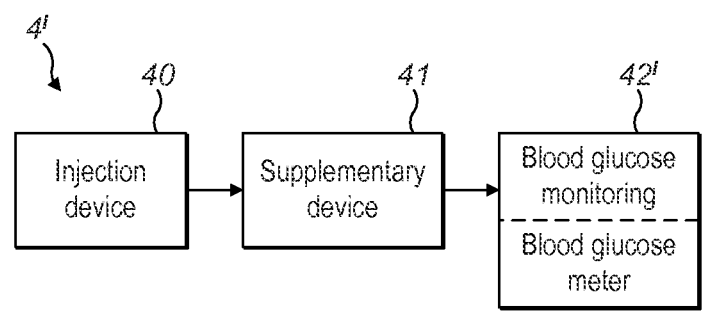

FIGS. 3A and 3b show possible distributions of functions among devices when using a supplementary device (such as the supplementary device of FIGS. 2a and 2b) together with an injection device.

In constellation 4 of FIG. 3a, the supplementary device 41 (such as the supplementary device of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as a desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification. Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

Figure 4:
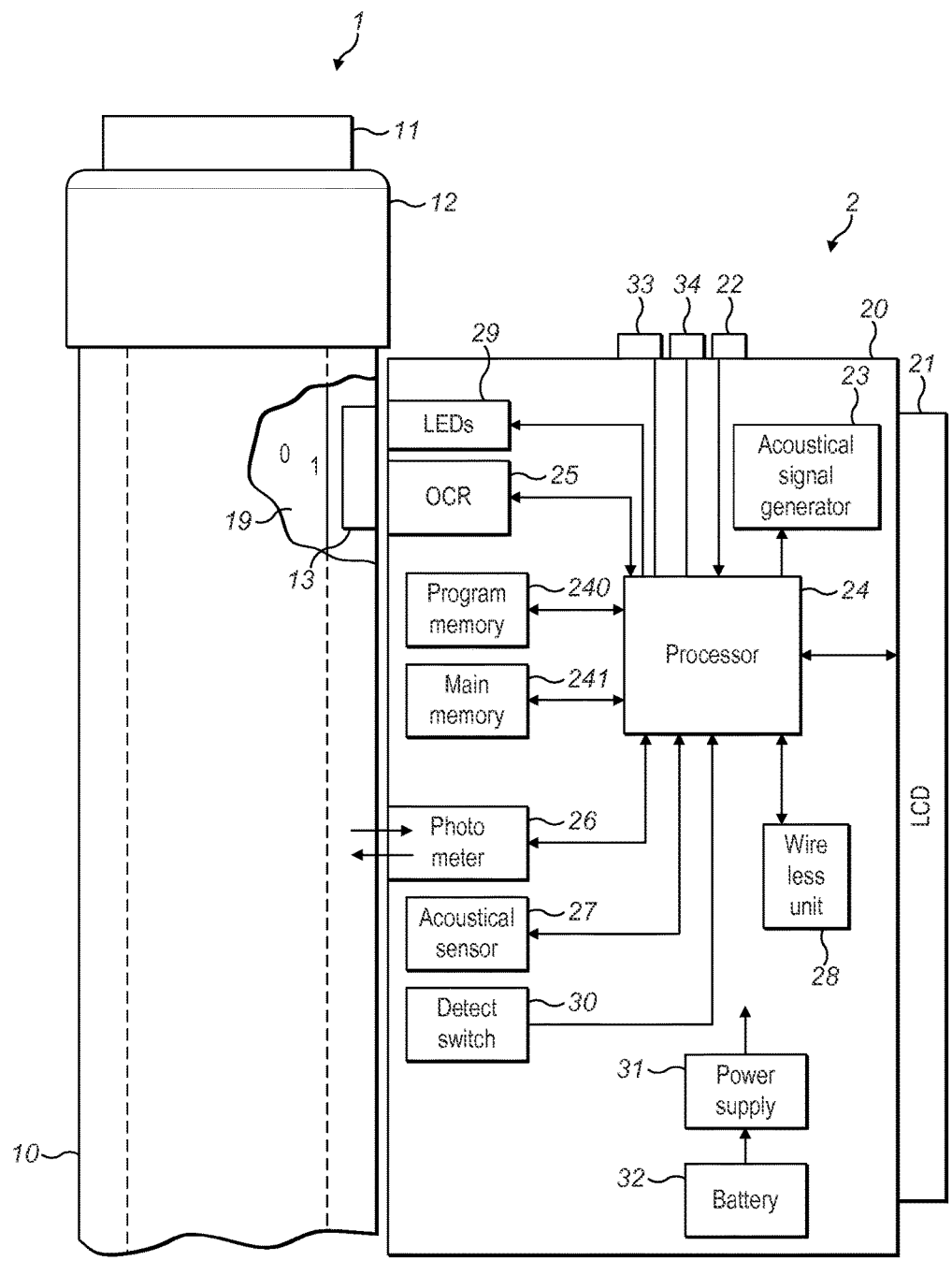
FIG. 4: a schematic view of the supplementary device of FIG. 2 in a state where it is mounted to the injection device of FIG. 1.

FIG. 4 shows a schematic view of the supplementary device 2 of FIGS. 2a and 2b in a state where it is attached to injection device 1 of FIG. 1.

With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In an example embodiment, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. The buttons 22, 33, 34 may be any suitable form of user input transducers, for instance mechanical switches, capacitive sensors or other touch sensors.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage display 13, in which a currently selected dose is displayed (by way of numbers printed on the sleeve 19 contained in injection device 1, which numbers are visible through the dosage display 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage display 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through an opening or window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage display 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 5A:
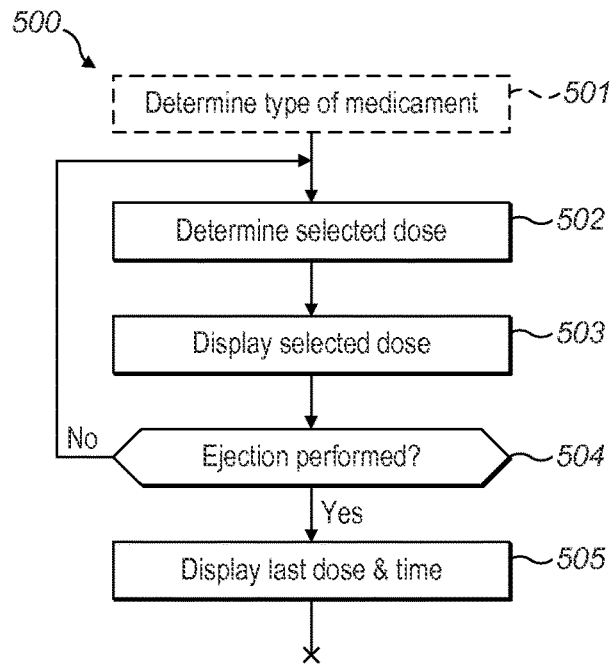
FIG. 5a: a flowchart of a method used in various embodiments.
Figure 5B:
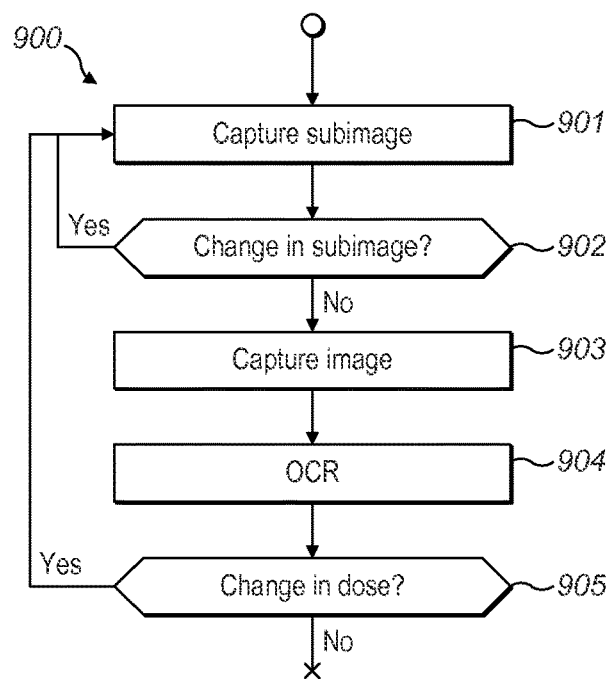
FIG. 5b: a flowchart of a further method used in a various embodiments.
Figure 5C:
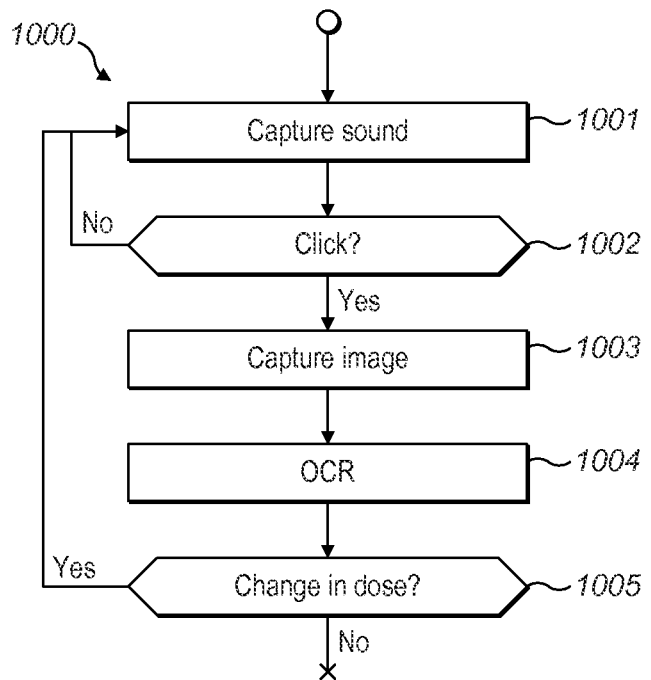
FIG. 5c: a flowchart of another method used in various embodiments.

FIGS. 5a-5c are flowcharts of embodiments of methods according to the present invention. These methods may for instance be performed by processor 24 of supplementary device 2 (see FIGS. 2b and 4), and may for instance be stored in program memory 240 of supplementary device 2, which may for instance take the shape of tangible storage medium 60 of FIG. 6.

FIG. 5a shows method steps that are performed in scenarios as shown in FIGS. 3a and 3b, where information read by supplementary device 41 (such as the supplementary device of FIGS. 2a and 2b) from injection device 40 (such as the injection device 1 of FIG. 1) is provided to blood glucose monitoring system 42 or 42' without receiving information back from blood glucose monitoring system 42 or 42'.

The flowchart 500 starts for instance when the supplementary device is turned on or is otherwise activated. In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage display of injection device as described above. This information is then displayed to a user of the injection device in a step 503.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is stored in the main memory 241, from where it may later be transmitted to another device, for instance a blood glucose monitoring system. If a differentiation has been made concerning the nature of the ejection, for instance if the ejection was performed as a prime shot or as an actual injection, this information may also be stored in the main memory 241, and possibly later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, the flowchart 500 terminates.

FIG. 5c shows in more detail exemplary method steps that are performed when the selected dose is determined based on the use of optical sensors only. For instance, these steps may be performed in step 502 of FIG. 5a.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by way of numbers and/or a scale printed on the sleeve 19 of injection device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of injection device 1 which is visible through dosage window 13. After capturing an image, it is, for instance, further processed as follows:

- Division by a previously captured background image;
- Binning of the image(s) to reduce the number of pixels for further evaluations;
- Normalization of the image(s) to reduce intensity variations in the illumination;
- Sheering of the image(s); and/or
- Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplementary device 2. The captured image is for instance an image of the dosage window 13 of injection device 1, in which a currently selected dose is displayed (e.g. by way of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

FIG. 5c shows in more detail method steps that are performed when the selected dose is determined based on the use of acoustical and optical sensors. For instance, these steps may be performed in step 502 of FIG. 5a.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialled by turning dosage knob 12 of injection device 1 and/or when a dose is ejected/injected by pressing injection button 11, and/or when a prime shot is performed. If the captured sound is not a click sound, step 1001 is repeated. Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5c when it comes to power consumption of the supplementary device, because permanently capturing images or sub-images as shown in FIG. 5b typically is more power consuming than listening to an acoustical sensor such as a microphone.

Figure 6:
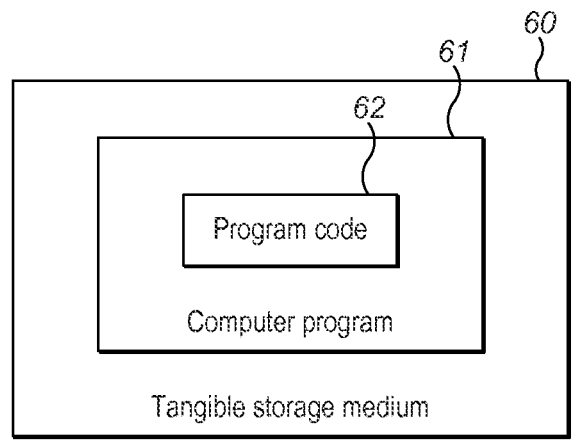
FIG. 6: a schematic illustration of a tangible storage medium 60 according to an embodiment of the present invention.

FIG. 6 is a schematic illustration of a tangible storage medium 60 (a computer program product) that comprises a computer program 61 with program code 62 according to aspects of the present invention. This program code may for instance be executed by processors contained in the supplementary device, for instance processor 24 of supplementary device 2 of FIGS. 2a and 4. For instance, storage medium 60 may represent program memory 240 of supplementary device 2 of FIG. 4. Storage medium 60 may be a fixed memory, or a removable memory, such as for instance a memory stick or card.

Figure 7:
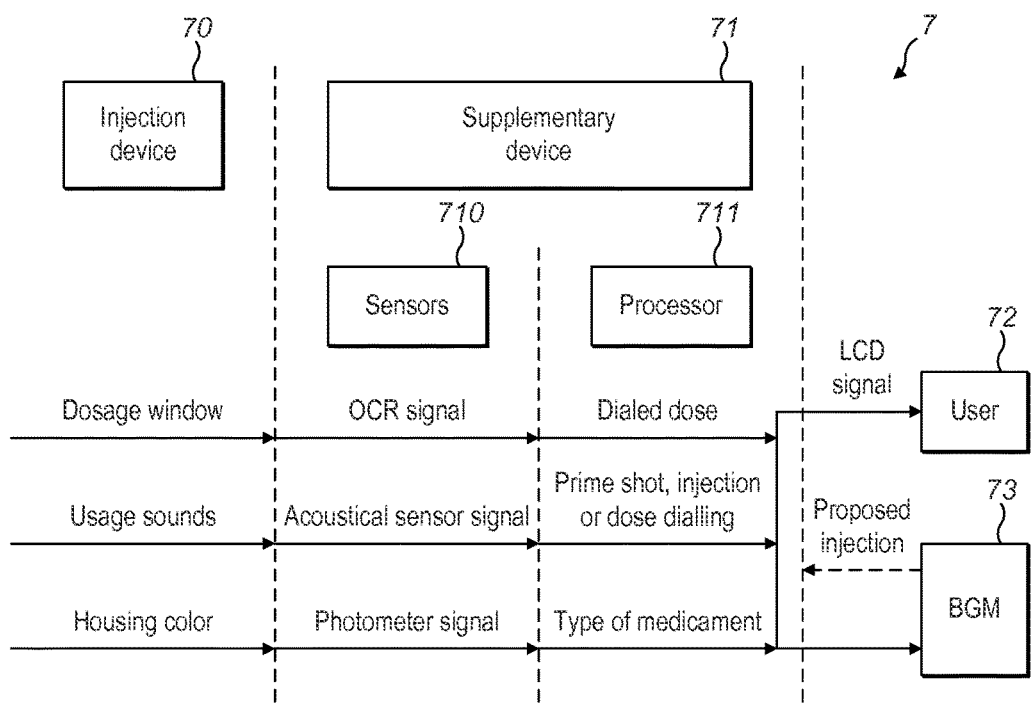
FIG. 7: an information sequence chart that illustrates an information flow between various devices according to embodiments of the invention.

Finally, FIG. 7 is an information sequence chart 7 that illustrates the flow of information between various devices (e.g. the injection device 1 and the supplementary device 2 of FIG. 4 in a scenario as depicted in FIG. 3a or 3b) according to an embodiment of the present invention. A condition and/or use of injection device 70 affects an appearance of its dosage window, sounds generated by injection device 70 and a colour of the housing. This information is transformed by sensors 710 of supplementary device 71 into an OCR signal, an acoustic sensor signal and a photometer signal, respectively, which are in turn transformed into information on the dialled dose, on an injection/dialling operation and on the type of insulin by a processor 711 of supplementary device 71, respectively. This information is then provided by supplementary device 70 to a blood glucose monitoring system 73. Some or all of this information is displayed to a user 72 via the display 21.

As described above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen by way of the mating unit, as will be described in detail hereinafter. The supplementary device reads out the injected dose. It may also transfer it to a blood glucose monitoring system with insulin titration capabilities. For patients taking multiple insulins, the supplementary device recognizes the device structure to the insulin type and may also transmit this piece of information to the blood glucose monitoring system.

The mating unit for releasably mounting the supplementary device 2 to the injection device in a specific position relative to an outside surface of the injection device 1 will now be described in detail.

The correct alignment of the supplementary device 2 on the injection device 1 ensures that the OCR reader 25 is correctly aligned with the dosage window 13. Correct alignment allows correct operation and reliable readings. Ensuring that there can be correct alignment between the supplementary device 2 and the injection device 1 in use allows a simpler design for the OCR reader 25, in particular because it does not need to be designed to be able to accommodate different alignments between the devices 1, 2.

Figure 8:
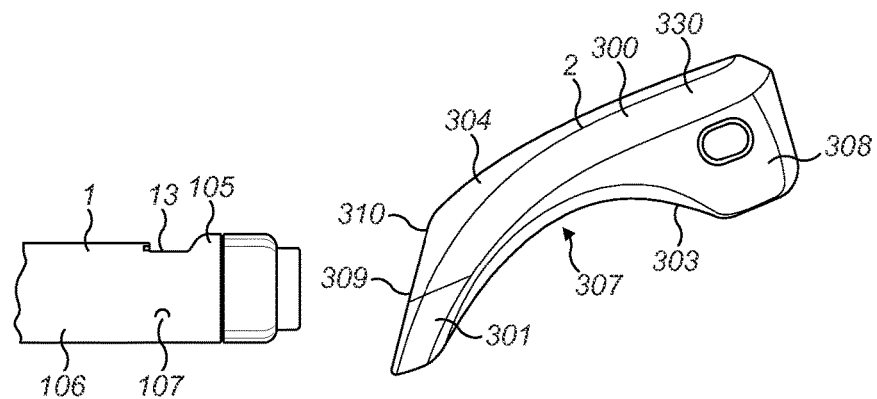
FIG. 8: a side view of the supplementary device shown in FIG. 2b orientated to be mounted to the injection device of FIG. 1.

Referring to FIG. 8, the supplementary device 2 is shown prior to mounting the supplementary device 2 on the injection device 1. In FIG. 8, the supplementary device 2 is shown orientated relative to the rear section 102 of the housing 10 of the injection device 1 so that the rear section 102 is receivable through the aperture 306 formed in the collar 301.

The housing 20 of the supplementary device 2 comprises the body 300 and the collar 301. The body 300 is elongate and has a longitudinal axis. The collar 301 distends downwardly from the front end 304 of the body 300.

The channel 307 formed in the lower side 303 of the body 300 extends from the aperture 306 (refer to FIG. 13) formed in the collar 301. Therefore, an upper portion of the aperture 306 forms part of the elongate channel extending between the front end 304 and the rear end 305 of the housing 20.

The aperture 306 has a front opening 309. The front opening 309 is formed in a front face 310 of the housing 20. The front face 310 may be planar. The edge of the front opening 309 is defined on a plane extending at an angle to the longitudinal axis of the elongate body 300. The front opening 309 has an elliptical shape. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. It will be understood that the rear section 102 of the injection device 1 is receivable through the opening 309 so that it extends through the aperture 306.

The channel 307 is shown in FIGS. 11 to 14. The channel 307 has a base 312. The base 312 of the channel 307 is arcuate in cross-section. The base 312 extends parallel to the longitudinal axis of the body 300. The shape of the base 312 corresponds to the outer surface of the rear section 102 of the injection device 1. Therefore, the rear section 102 of the injection device is receivable therein and the outer surface of the injection device 1 locates against the channel base 312. The optical sensor 25 (not shown in FIGS. 8 to 13) is embedded in the channel base 312 to face into the channel 312.

The collar 301 defines an upper part 314 and a lower part 315. The upper part 314 is integrally formed with the body 300 and thus extends from the base 312 of the channel 307. The lower part 315 opposes, but is at least partially offset from, the upper part 314. In the present embodiment, the upper part 314 is defined by the upper half of the inner surface of the collar 301 and the lower part 315 is defined by the lower half of the inner surface of the collar 301. The inner surface of the collar 301 defines a cylinder, with the base 312 of the channel 307 extending from the cylindrical surface. Therefore, the arcuate base of the channel 307 and the inner cylindrical surface of the collar are formed to arc about the same longitudinal axis.

A lower locating surface 317 is defined on the lower part 315 of the collar 301. An upper locating surface 316 is defined on the upper part 314 of the collar 301. The upper and lower locating surfaces 316, 317 oppose each other. When the injection device is received through the aperture, the upper and lower locating surfaces 316, 317 are configured to locate against the outer surface of the injection device 1. The locating surfaces 316, 317 are brought into contact with the injection device 1 by rotating the supplementary device 2 about an axis extending perpendicular to the major axis of the opening 309 so that the upper and lower locating surfaces are moved towards the outer surface of the injection device 1. The central axis of the cylindrical aperture 306 extending through the collar is brought into co-axial alignment with the longitudinal axis of the injection device 1.

Although in the present embodiment the collar 301 has a cylindrical arrangement, it will be understood that a break may be formed in the collar 301 to form two collar portions (not shown) with distal ends that distend towards each other, but are spaced from each other, so that the collar portions define a passage. A section of one or both of the collar portions defines the lower locating surface 317. Similarly, in an alternative arrangement an arcuate collar member (not shown) may extend from one side of the channel to define a channel and the lower locating surface 317.

In the present embodiment, the base 312 of the channel extends co-planer with the upper part of the collar 301. Therefore, the base 312 of the channel also locates against the outer surface of the injection device 1 when the supplementary device 2 is rotated about an axis extending perpendicular to the major axis of the opening 309 so that the upper and lower locating surfaces 316, 317 are moved to lie against the outer surface of the injection device 1. Therefore, it will be understood that the upper locating surface may be formed by the upper part of the collar 301, or by the base 312 of the channel 307. Alternatively, the lower locating surface 317 is formed on one or more locating elements protruding into the aperture from the lower part of the collar 301. Similarly, the upper locating surface 316 may be formed on one or more locating elements protruding into the aperture 306 or the injection device receiving channel 307.

A rib receiving recess 311 is formed in the base 312 of the channel 307. The rib receiving recess 311 is dimensioned to receive the rib 105 protruding from the outer surface 106 of the injection device 1. The rib receiving recess 311 is dimensioned so as to correspond closely to the shape and size of the locating rib 105 that is present on the injection pen 1. The rib receiving recess 311 is slightly larger than the locating rib 105 so as to ensure that the locating rib 105 can be easily located within the recess 311. Therefore, the rib receiving recess 311 acts as an alignment element for locating the body in a specific position relative to the outer surface 106 of the injection device 1 when the rib 105 is received in the rib receiving recess 311. The rib receiving recess 311 therefore aids the correct alignment and orientation of the body 300 on the injection device 1.

The rib receiving recess 311 is formed at the end of the supplementary device 2 that is closest to the dosage knob 12 when the supplementary device 2 is fitted to the injection device 1.

As described above, the supplementary device 2 comprises the supplementary device housing and the mating unit. The mating unit is configured to embrace the housing 10 of injection device 1 of FIG. 1, so that supplementary device 2 sits tightly on housing 10 of injection device 1, but is nevertheless removable from injection device 1, for instance when the injection device 1 is empty and has to be replaced.

A first engaging arm 320 is pivotably mounted in the body 300 of the supplementary device 2. A second engaging arm 321 is pivotably mounted in the body 300 of the supplementary device 2. The first and second engaging arms 320, 321 are disposed on opposing sides of the body 300.

The first and second engaging arms 320, 321 extend from the injection device receiving channel 307. The first and second engaging arms 320, 321 extend from opposing sides of the channel 307 and are spaced from each other. The first and second engaging arms 320, 321 are disposed so that the supplementary device 2 is receivable therebetween.

Wings 308 depend from each side of the body 300. In FIGS. 11 to 14 one of the wings 308 is omitted. The wings 308 act as protective walls. Each wing 308 protrudes from the lower side 303 of the body 300. The body 300 has two opposing wings 308 which depend from opposing sides of the channel 307. The wings 308 may be integrally formed with the body 300. The wings 308 extend the side walls of the channel 307. In an alternative embodiment the wings 308 are omitted. However, in the present embodiment, the wings 308 extend over the mating elements 320, 321. Therefore, the wings 308 act as protective elements.

The first and second engaging arms 320, 321 are elongate members. The first engaging arm 320 is pivotably mounted to the body 300 of the supplementary device 2 by a first pivot axle 322. The second engaging arm 321 is pivotably mounted to the body 300 of the supplementary device 2 by a second pivot axle 323. The first pivot axle 322 is a cylindrical shaft protruding from opposing sides of the first engaging arm 320. The second pivot axle 323 is a cylindrical shaft protruding from opposing sides of the second engaging arm 321. The first and second pivot axles 322, 323 extend perpendicular to the longitudinal axes of the first and second engaging arms 320, 321 respectively.

An engaging part 324 of the first engaging arm 320 extends from the first pivot axle 322. A release part 325 of the first engaging arm 320 extends from the opposing side of the first pivot axle 322. The engaging part 324 and release part 325 together form the first engaging arm 320. The first pivot axle 322 is disposed at a midsection of the first engaging arm 320.

An engaging part 326 of the second engaging arm 321 extends from the second pivot axle 323. A release part 327 of the second engaging arm 321 extends from the opposing side of the second pivot axle 323. The engaging part 326 and release part 327 together form the second engaging arm 321. The second pivot axle 323 is disposed at a midsection of the second engaging arm 321.

In the present embodiment, the first and second pivot axles 322, 323 are fixedly mounted to the respective first and second engaging arm 320, 321 so that each arm 320, 321 and corresponding pivot axle 322, 323 rotate together in the body 300. In such an arrangement, the opposing ends of the pivot axles 322, 323 are received in receiving holes in the body 300 in which the ends are able to rotate. Therefore, the pivot axles 322, 323 and engaging arms 320, 321 are able to pivot in the body 300. In such an embodiment the pivot axles 322, 323 are fixedly mounted to the engaging arms 320, 321. However, in an alternative embodiment the first and second engaging arms 320, 321 are rotatable about their respective pivot axles 322, 323. In such an arrangement, the pivot axles 322, 323 may be fixedly mounted to the body 300.

The first engaging arm 320 has a first protuberance 328 disposed at a free end 329 of the engaging part 324 of the first engaging arm 320. The second engaging arm 321 has a second protuberance 330 disposed at a free end 331 of the engaging part 324 of the second engaging arm 321. Each protuberance 328, 330 acts as an engaging element to engage in the indents 107 formed in the outer surface of the rear section 102 of the injection device 1. The first protuberance 328 on the first engaging arm 320 is configured to be received in the left indent 107. The second protuberance 330 on the second engaging arm 321 is configured to be received in the right indent 107. The protuberances 328, 330 are shaped to correspond to the shapes of the indents 107 respectively. In this way, the protuberances 328, 330 fit within the corresponding indents 107 respectively when the supplementary device 2 is correctly positioned on the injection device 1. The external dimensions of the protuberances 328, 330 are slightly smaller than the internal dimensions of the indents 107 so as to ensure that the protuberances 322 fit within their respective indent. Therefore, indents 107 act as engaging portions.

Figure 15:
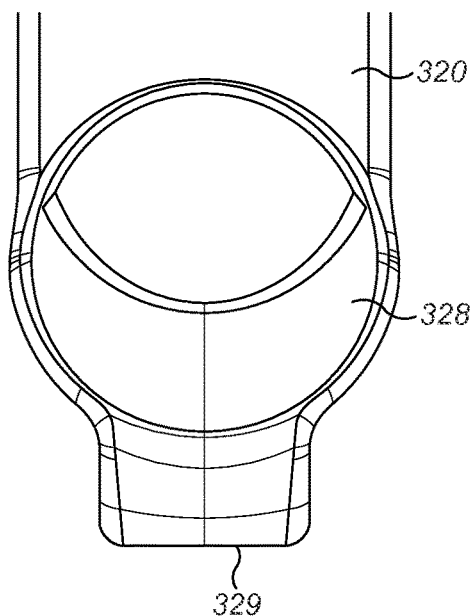
FIG. 15: a lower end of the first engaging arm with a first protuberance.
Figure 16:
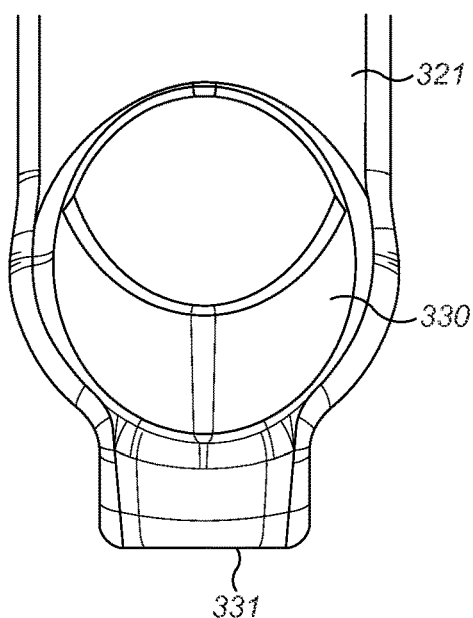
FIG. 16: a a lower end of the second engaging arm with a second protuberance.

In the present embodiments, the first protuberance 328 is shaped to correspond closely to the shape of the left indent 107, as shown in FIG. 15. In this way, the first protuberance 328 fits snugly within the left indent 107 when the supplementary device 2 is correctly positioned on the injection pen 1. The second protuberance 330 is shaped similarly to the first protuberance 328, although the width of the second protuberance 330 is smaller width than the width of the first protuberance 328. In the present arrangement, this is achieved with an "almond" shaped geometry, as shown in FIG. 16. This is the reason for the end face of the first protuberance 328 having a larger area than the second protuberance 330. The different sizes for the protuberances 328, 330 helps the protuberances find engagement within the indents 107. The first protuberance 328 can be considered to be a master to the second protuberance 330, which is a slave. However, it will be understood that in an alternative embodiment the protuberances 328, 330 are identical.

Although the engaging elements on the first and second engaging arms 320, 321 are formed by protuberances which are configured to be received in corresponding indents 107 on the injection device, it will be understood that alternative arrangements are envisaged. For example, in an alternative arrangement the engaging element on one or both of the engaging elements 320, 321 is formed by a notch or indent formed proximate to the free end 329, 330 of the or each engaging element 320, 321 which is configured to locate over and/or receive a corresponding protrusion or ledge on the injection device 1 so that the engaging arms 320, 321 engage with the injection device 1.

The release part 325 of the first engaging arm 320 has a first actuating section 333 at its distal end to the pivot axle 322. The first actuating section 333 is disposed on the opposing side of the first engaging arm 320 to the first protuberance 328. The first actuating section 333 is disposed at an opposing end of the first engaging arm 320 to the first protuberance 328.

The release part 327 of the second engaging arm 321 has a second actuating section 334 at its distal end to the second pivot axle 323. The second actuating section 334 is disposed on the opposing side of the second engaging arm 321 to the second protuberance 330. The second actuating section 334 is disposed at an opposing end of the second engaging arm 321 to the second protuberance 330.

The actuating sections 333, 334 are formed by upstanding portions or stepped portions of the engaging arms 320, 322. Each actuating section 333, 334 has an outer face against which a user is able to act, as will become apparent hereinafter. The actuating sections 333, 334 are configured to extend through the body 300 of the supplementary device 2 on opposing sides of the body 300 so that they are exposed on an outer side. Therefore, a user is able to urge the engaging arms 320, 322 to pivot.

The first engaging arm 320 is received in a one side of the body 300. The second engaging arm 321 is received in an other side of the body 300. The engaging arms 320, 321 are disposed behind the wings 308 that depend from the body 300. The wings 308 may be formed from a transparent material. This allows a user to be able to view the locations of the engaging arms 320, 321 relative to the indents 107, which may help the user to locate the supplementary device 2 correctly on the injection device 1. As can be seen from FIGS. 11 to 14, the wings 308 extend slightly further in a downwards direction than the engaging arms 320, 321. The engaging arms 320, 322 are rotatably mounted in the body 300 by the pivot axles 322, 323.

The first engaging arm 320 is received in a first arm receiving space 335 on one side of the body 300 and the second engaging arm 321 is received in an arm receiving space 335 on one side of the body 300. The engaging parts 324, 326 of the engaging arms 320 extend through gaps 336 in the channel base 312 so that they face into the channel 307 from opposing sides of the channel base 312. This is the engaging parts 324, 326 of the engaging arms 320 are able to protrude into the channel 307 from the gaps 336.

A first torsion spring 338, acting as a resilient member, acts on the first engaging arm 320. The first torsion spring 338 acts on the first engaging arm 320 to urge the first engaging arm 320 to rotate. The first torsion spring 338 biases the engaging part 324 of the first engaging arm 320 to protrude into the channel 307. In the present embodiment, the first torsion spring 338 acts on the engaging part 324 to bias the first engaging arm 320, however it will be understood that the first torsion spring 338 may act on the release part 325.

A second torsion spring 339, acting as a resilient member, acts on the second engaging arm 321. The second torsion spring 339 acts on the second engaging arm 321 to urge the second engaging arm 321 to rotate. The second torsion spring 339 biases the engaging part 326 of the second engaging arm 321 to protrude into the channel 307. In the present embodiment, the second torsion spring 339 acts on the engaging part 326 to bias the second engaging arm 321, however it will be understood that the second torsion spring 339 may act on the release part 326.

The first and second torsion springs 338, 339 are disposed on the first and second pivot axles 322, 323 respectively (in particular, refer to FIGS. 11 to 13, and 17). Therefore, a compact arrangement is achieved. One end of each torsion spring 338, 339 acts on the body 300 of the supplementary device 2 and the other end acts on the corresponding engaging arm 320, 321. The end of each torsion spring 338, 339 acting on the engaging arms 320, 321 has a protruding leg 338a, 339a which acts on a rear side of the corresponding engaging arm 320, 321. The protruding legs 338a, 339a of each torsion spring 338, 339 are received in a corresponding notch 343 on the rear side of the corresponding engaging arm 320, 321. In an alternative embodiment one end of the torsion springs 338, 339 acts on the pivot axles 322, 323 to cause the engaging arms 320, 321 to rotate.

In the present arrangement each torsion spring 338a, 339a is configured to impart an urging force on the corresponding engaging arm in the range of 2N to 10N. Preferably, the urging force imparted on each engaging arm is in the range of 3N to 7N, and more preferably in the range of 4N to 5N. However, it will be understood that the urging force imparted by each engaging arm is dependent on the relationship of the engaging arm and the requirements regarding attachment force and detachment force.

Figure 13:
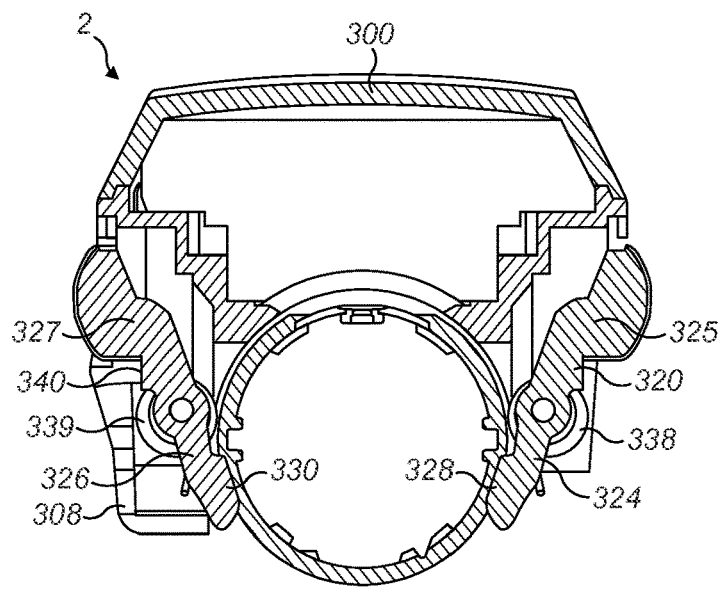
FIG. 13: a cross-sectional view from the front of the supplementary device shown in FIG. 2b with a wing omitted releasably attached to the injection device of FIG. 1 with resilient arms of a fixing unit in an engaged position with the injection device.
Figure 14:
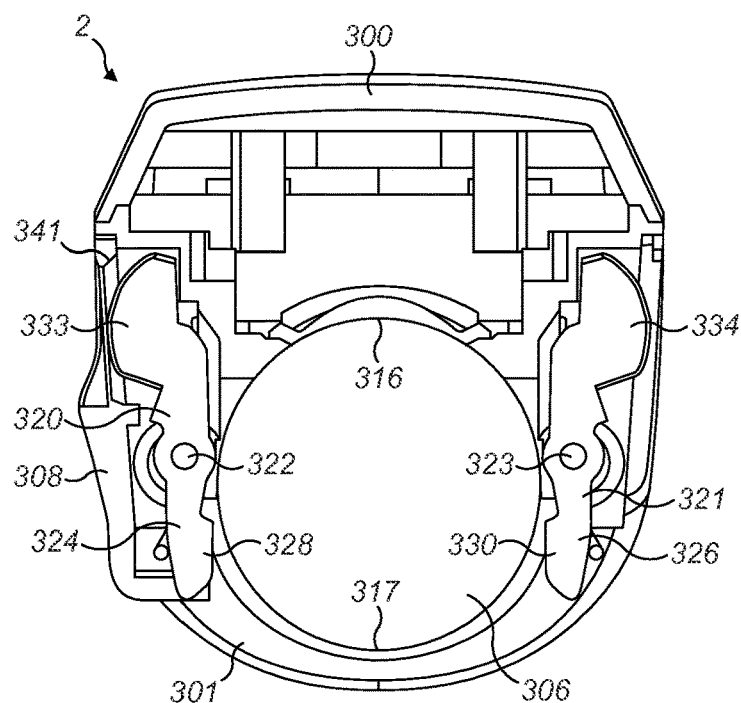
FIG. 14: a cross-sectional view from the front of the supplementary device shown in FIG. 2b with a wing omitted detached from the injection device of FIG. 1 with resilient arms of the fixing unit in a disengaged position.
Figure 17:
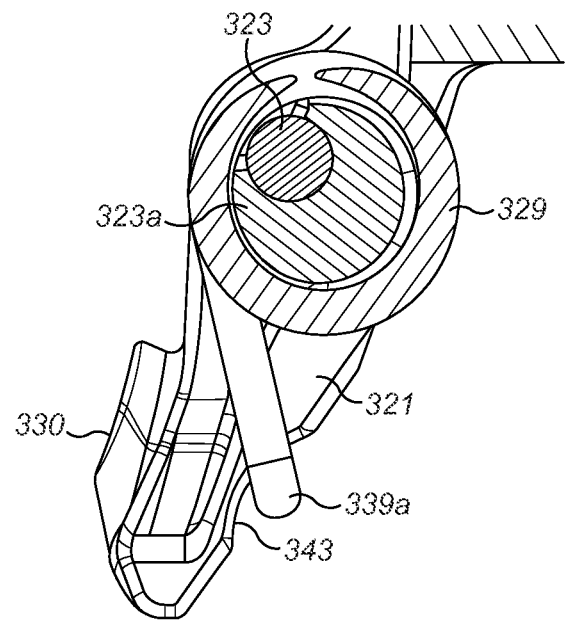
FIG. 17: a cross-sectional view of part of the supplementary device shown in FIG. 2b showing the second engaging arm received on a pivot axle.

Referring to FIGS. 13 and 17, the central axis defining the rotational axis of each torsion spring 338a, 339a is offset from the rotational axis of the corresponding pivot axles 322, 323, and therefore the rotational axis of the engaging arms 320, 321, eccentric members are mounted on the pivot axles to eccentrically mount the torsion springs around the pivot axles. For example, in FIG. 17 an eccentric member 323a is mounted on the second pivot axle 323. The second pivot axle 323 is disposed proximate to a circumferential edge of the eccentric member 323a. The second torsion spring 338b extends around the eccentric member 323a. Although in the present embodiment the eccentric members are mounted to the corresponding pivot axle, it will be understood that in an alternative embodiment the or each eccentric member may be integrally formed with the corresponding pivot axle. The positioning of the rotational axis of the torsion springs 338a, 339a offset from the rotational axis of the pivot axles ensures that the angle under which the protuberances 328,330 are urged into the indents 107 is kept flat so that the holding force in a radial direction is maximised.

Figure 12:
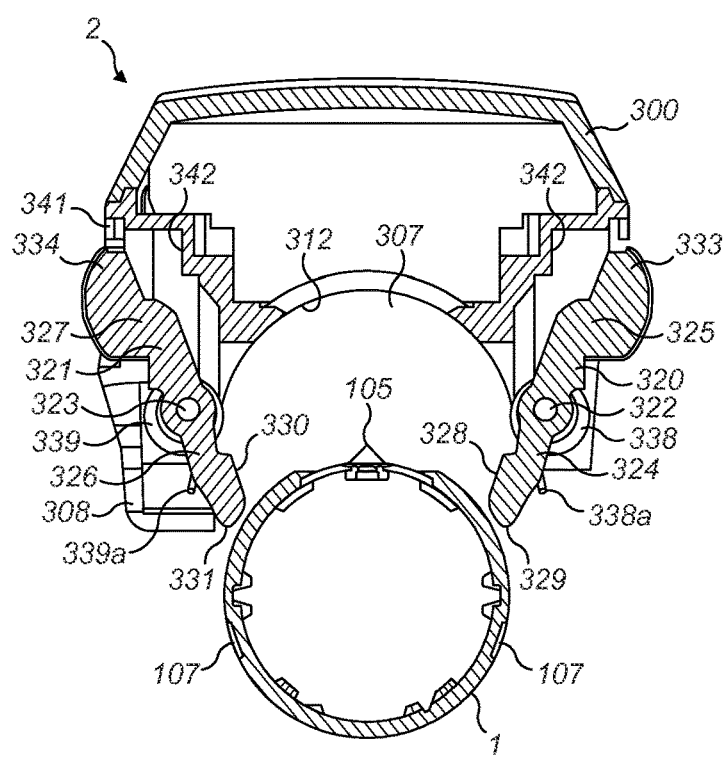
FIG. 12: a cross-sectional view from the front of the supplementary device shown in FIG. 2b showing first and second engaging arms, and with a wing omitted detached from the injection device of FIG. 1.

The engaging parts 324, 326 of the engaging arms 320, 321 are splayed towards each other. The effect of the resilience of the torsion springs 338, 339 is to bias the engaging part 324, 326 of each arm 320 into a certain position. The position into which the engaging part 324, 326 of each engaging arm 320, 321 is a disengaged position (refer to FIG. 12), wherein they are initially located such that the distance between the innermost surfaces of the protuberances 328, 330 at the free end 329, 331 of the arms 320, 321 is slightly less than the distance between the bottoms of the indents 107. The effect of the bias of the torsion springs 338, 339 of each arm 320, 321 is to resist movement of the protuberances 328, 330 and the engaging parts 324, 326 of the arms 320, 321 away from one another. End stops 340 are formed in the body 300 to limit rotation of the engaging arms 320, 321. The arms 320, 321 act against the end stops 340 when the torsion springs 338, 339 bias the arms into their unengaged position, as shown in FIG. 12. In the present embodiment, the end stops 340 are formed by the wings 308.

The engaging arms 320, 321, acting as support members, are restrained from moving in a direction along the longitudinal axis of the elongate body 300. This assists in maintaining the supplementary device 2 in the correct location after engagement of the supplementary device on the injection pen 1 even in the presence of forces acting to move the supplementary device 2 along the longitudinal axis of the injection pen 1.

The actuating sections 333, 334 of the engaging arms form left and right buttons extending from opposing sides of the body 300. An aperture 341 is formed through each side of the body 300 through which the actuating sections 333, 334 of the engaging arms extend to protrude from the body 300 when the engaging arms 320, 321 are biased into their disengaged position, as shown in FIG. 12.

Although in the present embodiment the supplementary device 2 has first and second engaging arms 320, 321, it will be understood that in an alternative embodiment, the supplementary device 2 may have one engaging arm only. Alternatively, the supplementary device 2 may have a pivotable first engaging arm, and a second fixed engaging arm. An advantage of having two pivotable engaging arms is that they help ensure a correct engagement.

When the actuating sections 333, 334 are pressed inwardly by a user the engaging arms 320, 321 are urged to rotate about the pivot axles defining pivot axes of the engaging arms 320, 321. The arms 320, 321 act against the bias of the torsion springs 338, 339 so that the engaging parts 324, 326 move outwardly.

When a user applies a force to the actuating sections 333, 334 of the arms 320, 321, the arms 320, 321 pivot about their axis and the actuating sections 333, 334 move inwardly. The engaging parts 324, 326 of the two arms 320, 321 are urged to rotate about their respective pivot axles 322, 323. Therefore, the free ends 329, 331 of the arm engaging parts 324, 326 are urged away from each other into a detached position. The release of the pressing force on each actuating section 333, 334 releases the biasing force acting on each arm 320, 321 and so the engaging part of each arm is urged to return to its neutral position due to the resilience of the torsion springs 338, 339.

As is shown in FIG. 8, the supplementary device 2 is initially located with respect to the injection pen 1 such that the opening 309 to the aperture 306 in the collar 301 is aligned with the rear end of the injection device 1. The body 300 is orientated so that the longitudinal axis of the injection device receiving channel 307 is inclined with respect to the longitudinal axis of the injection device 1.

Figure 9:
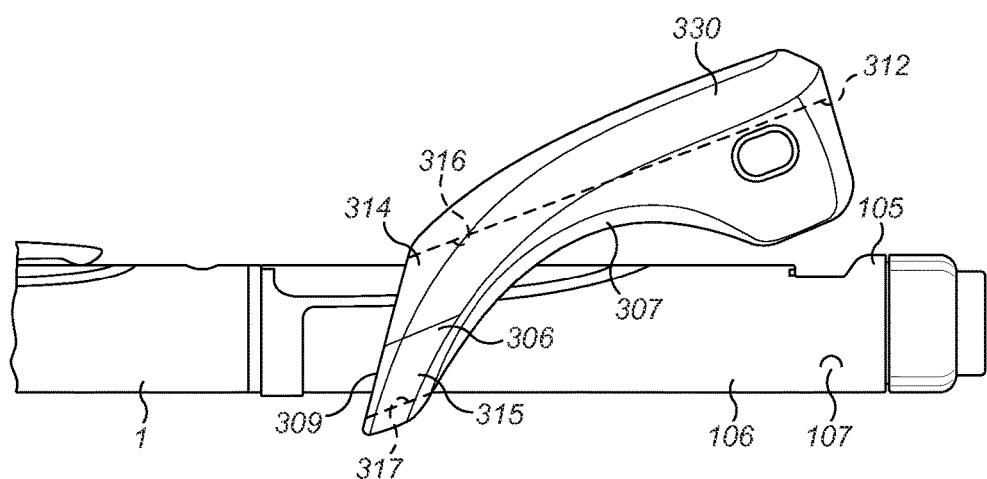
FIG. 9: a side view of the supplementary device shown in FIG. 2b with the injection device of FIG. 1 received through a collar of the supplementary device.

The collar 301 is then slid over the rear section 102 of the injection device 1, as shown in FIG. 9. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. Therefore, the rear section 102 of the injection device 1 is received through the aperture 306 of the collar 301.

In order to locate the supplementary device 2 on the injection device 1, the supplementary device 2 is rotated relative to the injection device 1 about an axis extending perpendicular to the major axis of the opening 309. The longitudinal axes of the injection device 1 and the injection device receiving channel 307 are rotated towards each other. Furthermore, the upper and lower locating surfaces 316, 317 are moved towards the outer surface of the injection device 1.

As the supplementary device 2 and injection device 1 are rotated relative to each other the free ends 329, 331 of the first and second engaging arms 320, 321, in particular the protuberances 328, 330, are brought into contact with the outer surface of the injection device housing 10. The protuberances 328, 330 here contact the housing to the left and right sides of the display window 13.

In order to engage the supplementary device 2 with the injection device 1, the user first arranges the supplementary device 2 with respect to the injection device 1 as shown in FIG. 9, and then applies a further force downwards on the supplementary device 2 while at the same time applying a force upwards on the injection device 1. Therefore, the supplementary device 2 and injection device 1 are urged to rotate relative to each other about the collar 301. A biasing force is therefore applied to the protuberances 328, 330 by the outer surface of the rear section 102 of the injection device 1. As the injection device 1 and the supplementary device 2 are urged to move closer together, the biasing force results in the arms being urged away from each other. The arms 320, 321 are urged to deflect outwardly, and to rotate about their pivot axes against the action of the torsion springs 338, 339. The torsion springs 338, 339 cause a reaction force to be applied on each arm due to the resilience of the torsion springs 338, 339, which resists entry of the injection device 1 into the injection device receiving channel 307. However, as the supplementary device 2 is further rotated over the injection device 1, the protuberances 328, 330 become aligned with the left and right indent 107 and, due to the resilience of the torsion springs 338, 339, engage with the indents 107, as shown in FIG. 13. The pivot axles help to ensure the correct alignment of the arms 320, 321 and therefore the protuberances with the indents 107.

As the supplementary device 2 engages the protuberances 328, 330 in the indents 107, the rear section 2 of the injection device 1 is received in the injection device receiving channel 207. The lower locating surface 317 of the collar 301 is urged into contact with a lower side of the outer surface of the injection device 1, and the upper locating surface 316 is urged into contact with an opposing side of the outer surface of the injection device 1. Once the protuberances 328, 330 engage in the indents 107, there is significant resistance to further movement of the supplementary device 2 relative to the injection device 1, due in part to the lower and upper locating surfaces 316, 317 abutting the outer surface of the injection device. The upper and lower locating surfaces 316, 317 are partially offset from each other, with the upper locating surface 317 being disposed between the lower locating surface and the protuberances 328, 330. The action of the torsion springs 338, 339 acts to urge the injection device 1 against the base 312 of the channel 307. Movement of the supplementary device 2 relative to the injection device 1 in the opposite direction is restricted by the action of the torsion springs 338, 339 and due to the protuberances 328, 330 being engaged in the indents 107.

It will be understood that the body 300 is mated to the injection device 1 by the collar 301 extending circumferentially around the injection device 1 at a front end of the body 300, and the protuberances 328, 330 engaging in the indents 107 at the rear end of the body 300.

In the event that the user places the supplementary device 2 onto the injection pen 1 at a location such that the supplementary device 2 is rotated slightly about its longitudinal axis relative to its desired position, the rib 105 will not be received in the rib receiving recess 311 in the body 300. In this case, the supplementary device 2 is prevented from being located fully over the injection pen 1 by the rib 105 resting against the base 312 of the channel 307, spaced from the correct location within the rib receiving recess 311. Furthermore, the protuberances 328, 330 will be urged against the outer surface of the rear section 102 of the injection device 1, but will not locate in the corresponding indents 107. A user would know that the supplementary device 2 had not mated correctly with the injection pen 1 because they would not have received any haptic feedback from the mating of the protuberances 328, 330 with the indents 107. They would also notice that the rear end of the supplementary device was separated from the injection device 1. To correctly locate the supplementary device 2 in position with respect to the injection device 1, a user can simply rotate the supplementary device 2 relative to the injection device 1 about the longitudinal axis of the injection device 1. As the supplementary device 2 and the injection device 1 move relative to one another, the locating rib and the rib receiving recess 311 become aligned with each other. At this point the protuberances 328, 330 also align with the indents 107 and engage therewith. Haptic feedback is therefore provided by the mating of the protuberances 328, 330 with the indents 107 and the user can determine that the supplementary device 2 and the injection device 1 are properly located with respect to one another.

Similarly, if the supplementary device 2 is not correctly aligned with the injection device 1 in a longitudinal direction, the rib 105 and rib receiving recess 311 will not be aligned and the rib will not locate in the recess 311. Furthermore, the protuberances 328, 330 will be offset from the indents 107. Relative movement of the supplementary device 2 and the injection device 1 in a direction along the longitudinal axis of the injection device 1 will cause the rib to locate in the recess 311 and the protuberances 328, 330 to locate in the indents 107. At this point, the supplementary device 2 and the injection device 1 are fully engaged with one another.

Figure 10:
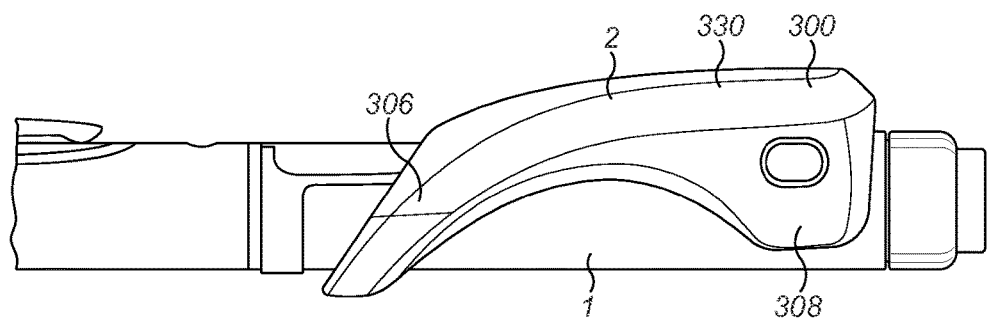
FIG. 10: a side view of the supplementary device shown in FIG. 2b releasably attached to the injection device of FIG. 1.

Once the protuberances 328, 330 are engaged in the indents 107, the injection device 1 is fully located within the injection device receiving channel 307 as shown in FIGS. 10 and 13. Here, the outermost surface of the display window 13 is aligned with a lowermost surface of the upper part of the supplementary device 2. The supplementary device 2 is shaped such that the injection device 1 fits snugly within the injection device receiving channel 307 and there are multiple points or areas of contact between the exterior surface of the housing 10 of the injection device 1 and the lowermost surface of the supplementary device 2 when the supplementary device and the injection pen 1 are in this relative position. When the supplementary device 2 is located with respect to the injection pen 1 such that the protuberances 322 are located within the indents 107 respectively, the rib 105 is engaged within the rib receiving recess 311. Correct alignment of the supplementary device 2 with respect to the injection device 1 is thus provided in two ways: firstly, by the location of the rib 118 within the rib receiving recess 311 and secondly by the locating of the protuberances 328, 330 within the indents 107.

It will be appreciated that the above arrangement prevents movement of the injection device 1 relative to the supplementary device 2. Movement of the supplementary device 2 in a radial direction from the injection device 1 is prevented by the collar 301 extending around the injection device 1. Movement of the supplementary device 2 in a radial direction from the injection device 1 is also prevented by the protuberances 328, 330 engaging in the indents 107. The engagement of the protuberances 328, 330 in the indents 107 also prevents movement of the supplementary device 2 along the longitudinal axis of the injection device 1 and about the longitudinal axis of the injection device 1. Additionally, movement of the supplementary device 2 about the longitudinal axis of the injection device and along the longitudinal axis of the injection device 1 is further prevented by the rib 105 being received in the rib receiving recess 311.

In order to remove the supplementary device 2 from the injection device 1, a user exerts a pressing force on the actuating sections 333, 334 of the engaging arms 320, 321 protruding from the outside of the body 300. The pressing force may be exerted by a finger and thumb. As the two actuating sections 333, 334 are depressed by the pressing force exerted by the user, engaging arms 320, 321 are urged to rotate about their axes.

Figure 18:
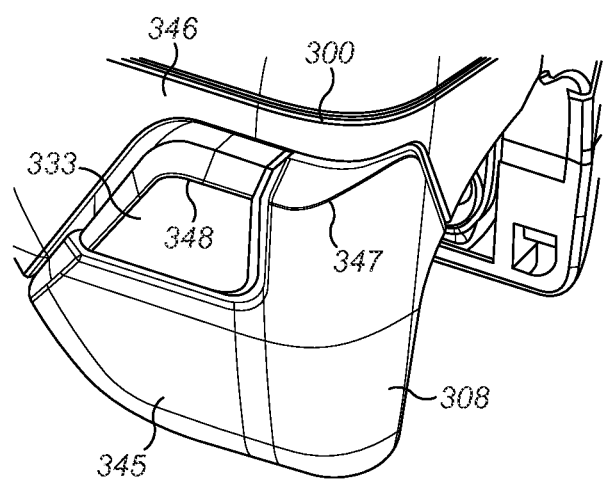
FIG. 18: a perspective view of part of the supplementary device shown in FIG. 2b.

Referring to FIG. 18, the actuating sections 333, 334 are configured to extend through the body 300 of the supplementary device 2 on opposing sides of the body 300 so that they are exposed on an outer side. The wings 308 are adjacent the actuating sections 333, 334. An outer surface 345 of each wing 308 protrudes from a body outer surface 346 and an edge 347 is defined along the outer surface 345 of each wing 308. The edge 347 forms a step. The actuating sections 333, 334 protrude from the body outer surface 346. However, the outer face of the relevant actuating section 333, 334 does not protrude from the outer surface 345 of the wing 308. That is, the outer face of the relevant actuating section 333, 334 lies planar with the outer surface 345 of the corresponding wing 308. An edge 348 of the corresponding actuating section 333, 334 extends from the edge 347 defined along the outer surface 345 of each wing 308. Therefore, accidental pressing or movement of the actuating sections 333, 334 is prevented by protruding design surfaces of the wings 308 which cover the button to the rear and the bottom sides.

The arms 320, 321 are urged to pivot about their pivot axles 322, 323. Therefore, the protuberances 328, 330 on each arm 320 are urged apart. This causes the protuberances 328, 330 to disengage from the indents 107. Therefore, the engaging arms 320, 321 move from their engaged position to their detached position. Rotation of the arms 320, 321 is limited by ends faces 342 against which the arms 320, 321 locate.

Once the protuberances 328, 330 have been urged from the indents 107, the user may then rotate the rear end of the supplementary device 2 away from the injection device 1 about an axis extending perpendicular to the major axis of the opening 309. As the protuberances 328, 330 are free of the indents 107, the user experiences relatively little resistance as the rear end of the body 300 is moved away from the injection device.

It will be understood that the cooperation between the rib 105 and the rib receiving recess 311 does not present any obstacle to separating the supplementary device 2 and the injection pen 1 in this way. The injection device 1 may then be slid from the aperture 306 formed in the collar 301.

Although in the above embodiment, the lower locating surface is defined by the lower part of the inner surface of the collar, it will be understood that the lower locating surface may be formed by another element on the lower part of the collar. Furthermore, a break may be formed in the collar.

Although in the above described embodiment the upper locating surface is defined by the upper part of the inner surface of the collar, it will be understood that the upper locating portion may be defined by the base of the channel. In such an arrangement, the inner surface of the collar and the base of the channel may be stepped from each other. The upper locating portion may be formed by another element on the upper part of the collar. Alternatively, the upper locating portion may be formed by another element on the base of channel.

Although the rib 105 and rib receiving recess aid orientation and alignment of the supplementary device 2 on the injection device 1 in the above described embodiments, it will be appreciated that in an alternative arrangement the rib 105 and rib receiving recess are omitted and the correct alignment between the supplementary device 2 and the injection device 1 is provided by mating of the protuberances and the indents 107.

Other alternative arrangements for ensuring a correct relative position between the supplementary device 2 and the injection device 1 will be envisaged by the skilled person, and all such alternatives are within the scope of the invention except when explicitly excluded by the language of the claims.

When using embodiments of the present invention, the user inter alia has the following advantages:

The user can use the most convenient disposable insulin injector.

The supplementary device is attachable and detachable (reusable).

The alignment unit ensures that the optical sensor is aligned with the dosage display. Therefore, a user does not have to manually orientate the supplementary device.

The engaging unit ensures that the supplementary device is securely mounted to the injection device 1. Therefore, the supplementary device does not inadvertently detach from the injection device.

The release arrangement allows the engaging unit to be easily disengaged from the injection device. This allows the supplementary device to be drawn away from the injection device without undue effort from a user. Furthermore, damage to the supplementary device and injection device is prevented during engagement and disengagement of the supplementary device to the injection device.

The invention claimed is:

1. A supplementary device for a manually operable injection device, the supplementary device comprising:
    a body; and
    a mating unit configured to releasably mount the body to the injection device in a specific position relative to an outside surface of the injection device,
    wherein the mating unit comprises:
        an engaging unit comprising an engaging arm configured to engage the supplementary device with the injection device and a resilient member configured to bias the engaging arm into engagement with the injection device, and
        a pivot axle defining a rotational axis about which the engaging arm is configured to rotate, wherein the resilient member is a torsion spring, and wherein a central axis defining the rotational axis of the torsion spring is offset from the rotational axis of the pivot axle.

2. The supplementary device of claim 1, wherein the engaging arm is rotatable between an engaged position and a detached position.

3. The supplementary device of claim 1, wherein the pivot axle extends perpendicular to the engaging arm.

4. The supplementary device of claim 1, wherein the resilient member is on the pivot axle.

5. The supplementary device of claim 1, wherein the resilient member is configured to act on the engaging arm proximate to or at a free end of the engaging arm.

6. The supplementary device of claim 1, wherein the engaging arm has an engaging element at one end configured to engage with a corresponding engaging portion on the injection device when the body is disposed in a specific position relative to the outside surface of the injection device.

7. The supplementary device of claim 6, wherein the engaging arm has an actuating section configured to urge the engaging element away from the injection device.

8. The supplementary device of claim 6, wherein the engaging arm has an actuating section configured to be operable such that the engaging element is moved from an engaged position to a detached position.

9. The supplementary device of claim 1, wherein the engaging arm is a first engaging arm and the engaging unit further comprises a second engaging arm, and wherein free ends of the first and second engaging arms are biased towards each other.

10. The supplementary device of claim 1, wherein the body comprises a channel configured to receive part of the injection device, wherein the engaging arm is configured to bias the injection device against a surface in the channel.

11. The supplementary device of claim 1, wherein the mating unit further comprises a collar extending from the body which is configured to receive the injection device so that the injection device extends through the collar.

12. The supplementary device of claim 11, wherein the mating unit further comprises first and second locating surfaces spaced from each other to receive the injection device therebetween, wherein the collar is configured to be pivoted between a first position in which the injection device is slidably receivable through the collar and a secured position in which the first and second locating surfaces are located against the outside surface of the injection device.

13. The supplementary device of claim 1, further comprising an optical reading arrangement and wherein the optical reading arrangement is directed at a display of the injection device when the body is mounted to the injection device in a position relative to the outside surface of the injection device.

14. The supplementary device of claim 1, wherein the resilient member is disposed eccentrically on the pivot axle.

15. The supplementary device of claim 14, further comprising an eccentric member mounted on the pivot axle to eccentrically mount the torsion spring around the pivot axle.

16. A system comprising:
    an injection devices; and
    a supplementary device comprising:
        a body, and
        a mating unit configured to releasably mount the body to the injection device in a specific position relative to an outside surface of the injection device,
        wherein the mating unit comprises:

an engaging unit comprising an engaging arm configured to engage the supplementary device with the injection device and a resilient member configured to bias the engaging arm into engagement with the injection device, and
a pivot axle defining a rotational axis about which the engaging arm is configured to rotate, wherein the resilient member is a torsion spring, and wherein a central axis defining the rotational axis of the torsion spring is offset from the rotational axis of the pivot axle.

* * * * *

UNITED STATES PATENT AND TRADEMARK OFFICE
CERTIFICATE OF CORRECTION

PATENT NO. : 10,195,355 B2
APPLICATION NO. : 14/783171
DATED : February 5, 2019
INVENTOR(S) : Alexander Allerdings, Martin Haupt and Erich Rittenbacher It is certified that error appears in the above-identified patent and that said Letters Patent is hereby corrected as shown below:

In the Claims

Column 24, Line 61, Claim 16, delete "devices;" and insert -- device; --

Signed and Sealed this
Twenty-sixth Day of May, 2020

Andrei Iancu
*Director of the United States Patent and Trademark Office*